US008564291B2

(12) United States Patent
Nelson et al.

(10) Patent No.: US 8,564,291 B2
(45) Date of Patent: Oct. 22, 2013

(54) FASTENER-LESS EDGE LAUNCH CONNECTOR FOR MR-COMPATIBLE MEDICAL MONITORING

(75) Inventors: Mark D. Nelson, Satellite Beach, FL (US); Eduardo M. Rey, Winter Springs, FL (US); Robert A. Harwell, St. Cloud, FL (US)

(73) Assignee: Koninklijke Philips N.V., Eindhoven (NL)

( * ) Notice: Subject to any disclaimer, the term of this patent is extended or adjusted under 35 U.S.C. 154(b) by 520 days.

(21) Appl. No.: 12/919,830

(22) PCT Filed: Feb. 2, 2009

(86) PCT No.: PCT/IB2009/050421
§ 371 (c)(1),
(2), (4) Date: Aug. 27, 2010

(87) PCT Pub. No.: WO2009/107010
PCT Pub. Date: Sep. 3, 2009

(65) Prior Publication Data
US 2011/0012597 A1    Jan. 20, 2011

Related U.S. Application Data

(60) Provisional application No. 61/032,530, filed on Feb. 29, 2008.

(51) Int. Cl.
*G01R 33/44* (2006.01)
(52) U.S. Cl.
USPC .............................. 324/309; 324/322; 439/83
(58) Field of Classification Search
USPC ........... 324/307–309; 600/410; 439/327–329, 439/581
See application file for complete search history.

(56) References Cited

U.S. PATENT DOCUMENTS

| 4,530,561 | A |   | 7/1985  | Tyree et al.           |
|-----------|---|---|---------|------------------------|
| 4,717,218 | A |   | 1/1988  | Ratcliff               |
| 4,826,447 | A |   | 5/1989  | Forker et al.          |
| 6,052,614 | A | * | 4/2000  | Morris et al. ... 600/509 |
| 6,341,988 | B1|   | 1/2002  | Zhu et al.             |
| 6,679,733 | B2| * | 1/2004  | Crane et al. ... 439/660 |
| 6,955,564 | B2| * | 10/2005 | Cho et al. ... 439/581   |
| 2002/0137385 | A1 |   | 9/2002  | Goodrich et al.      |
| 2003/0068914 | A1 |   | 4/2003  | Merry et al.         |
| 2004/0018766 | A1 | * | 1/2004  | Wu ... 439/327       |
| 2006/0293585 | A1 | * | 12/2006 | Beck ... 600/410     |
| 2007/0118032 | A1 |   | 5/2007  | Finneran et al.      |
| 2007/0257674 | A1 |   | 11/2007 | Gao et al.           |
| 2008/0003847 | A1 |   | 1/2008  | Lappoehn             |

FOREIGN PATENT DOCUMENTS

| DE | 3346866 A1       | 7/1985  |
| DE | 102006019891 A1  | 11/2007 |
| EP | 0262432 A1       | 9/1987  |
| EP | 0755653 A1       | 1/1997  |

* cited by examiner

*Primary Examiner* — Patrick Assouad
*Assistant Examiner* — Rishi Patel

(57) ABSTRACT

A robust MR compatible ECG monitor (40) includes a connector (50) for connecting ECG electrode leads (44) to an internal circuit board (52). The connector (50) includes connector pins (54) that run parallel to the circuit board (52) and tangentially contact solder pads (56) of the circuit board (52) at the edge of the circuit board (52), eliminating sharp or right angle turns in conduction paths. The connector prevents movement of the connections due to mechanical stresses in all ranges of motion relative to four degrees of freedom, including translation, pitching, yawing, and rolling.

14 Claims, 5 Drawing Sheets

US 8,564,291 B2

FASTENER-LESS EDGE LAUNCH CONNECTOR FOR MR-COMPATIBLE MEDICAL MONITORING

CROSS REFERENCE TO RELATED APPLICATIONS

This application claims the benefit of U.S. provisional application Ser. No. 61/032,530 filed Feb. 29, 2008, which is incorporated herein by reference.

The present application relates to the diagnostic arts. It finds particular application in increasing the usability of an electrocardiogram (EKG or ECG) monitor in a magnetic resonance environment, and will be described with particular reference thereto. It is to be understood, however, that the present application is applicable to X-ray and CT compatible instruments, EEG instrumentation, and all situations where low susceptibility to large external transients such as electrostatic discharge, defibrillator discharges, or RF emissions is required, and is not necessarily limited to the aforementioned application ECG monitoring of patients undergoing procedures in a magnetic resonance environment presents significant challenges of dealing with interference sources. Filtering is used to strip the MRI's RF energy from the raw ECG signals of the patient so that they can be reconstructed into an ECG waveform useful to a physician. The physical and electrical characteristics of the conductive path between the patient and the sensor (ECG leads) are specialized for sensors that are MR compatible. Sharp corners, acute and 90° angles, and changes in material can make a circuit more vulnerable to electromagnetic interference intrusion and exacerbate emissions. Wires are typically added to make the connection from the ECG connector block to the printed circuit board. The additional wiring complicates the circuit, and creates extra solder joints that can potentially fail.

Devices occasionally use an edge launch scheme for high frequency applications, in applications with a high sensitivity to manufacturing variations, or where a high signal-to-noise ratio is required. Typically, RF connectors incorporate one or more right angles in the conductive path to facilitate thru-hole assembly or other conventional connector attachment schemes. These right angle turns increase the inductances of the connections, increasing the potential for interference with the ECG signals by the RF fields.

Also, devices that use an edge launch scheme typically attach the connection block to the PCB using some type of threaded metallic fastener. Threaded metallic fasteners, even if non-magnetic, impact performance of the device being used in the magnetic field. Separate fasteners, whether metallic or non-metallic, complicate assembly of the connector.

The present application provides a new and improved edge launch connector which overcomes the above-referenced problems and others.

In accordance with one aspect, a magnetic resonance system is provided. A main magnet generates a substantially uniform main magnetic field in an examination region. A gradient coil assembly imposes gradient magnetic fields on the main magnetic field in the examination region, spatially encoding the main magnetic field. A radio frequency assembly induces magnetic resonance in selected dipoles of a subject in the examination region, and receives the magnetic resonance. A monitor analyzes signals originating from sensors in the examination region. The monitor includes a connector for providing an interface between sensor leads and a printed circuit board within the monitor. Electrical connector pins of the connector mate with solder pads of the circuit board at an edge of the circuit board.

In accordance with another aspect, a method of monitoring a subject in a magnetic field is provided. A main magnetic field is generated with a main magnet of a magnetic resonance imaging device. Gradient magnetic fields are applied to the examination region with a gradient coil system. RF pulses are applied to the examination region with an RF assembly. At least one parameter of the subject's physiology is monitored with sensors attached to the subject. Information is communicated from the sensors to a monitor over leads that interface with the monitor via a connector. The connector includes connector pins that interface tangentially with solder contacts of a circuit board of the monitor.

In accordance with another aspect, an electrocardiogram monitor is provided. At least one printed circuit board carries operational electronics of the monitor. A connector connects external sensor leads to the circuit board. The connector includes connector pins that tangentially engage an edge of the circuit board at solder pads.

One advantage lies in increased tolerance of large external transients.

Another advantage lies in increased resistance to electromagnetic interference.

Another advantage lies in a more robust connection of lead wires to a printed circuit board.

Another advantage lies in decreased circuit complexity.

Another advantage lies in the elimination of connection wires from the lead connector to the circuit board.

Another advantage lies in the lack of threaded and/or metallic fasteners.

Another advantage lies in the ability to use simplified filters, reducing production costs.

Another advantage is that incorrect connection of the connector to the circuit board is prevented.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
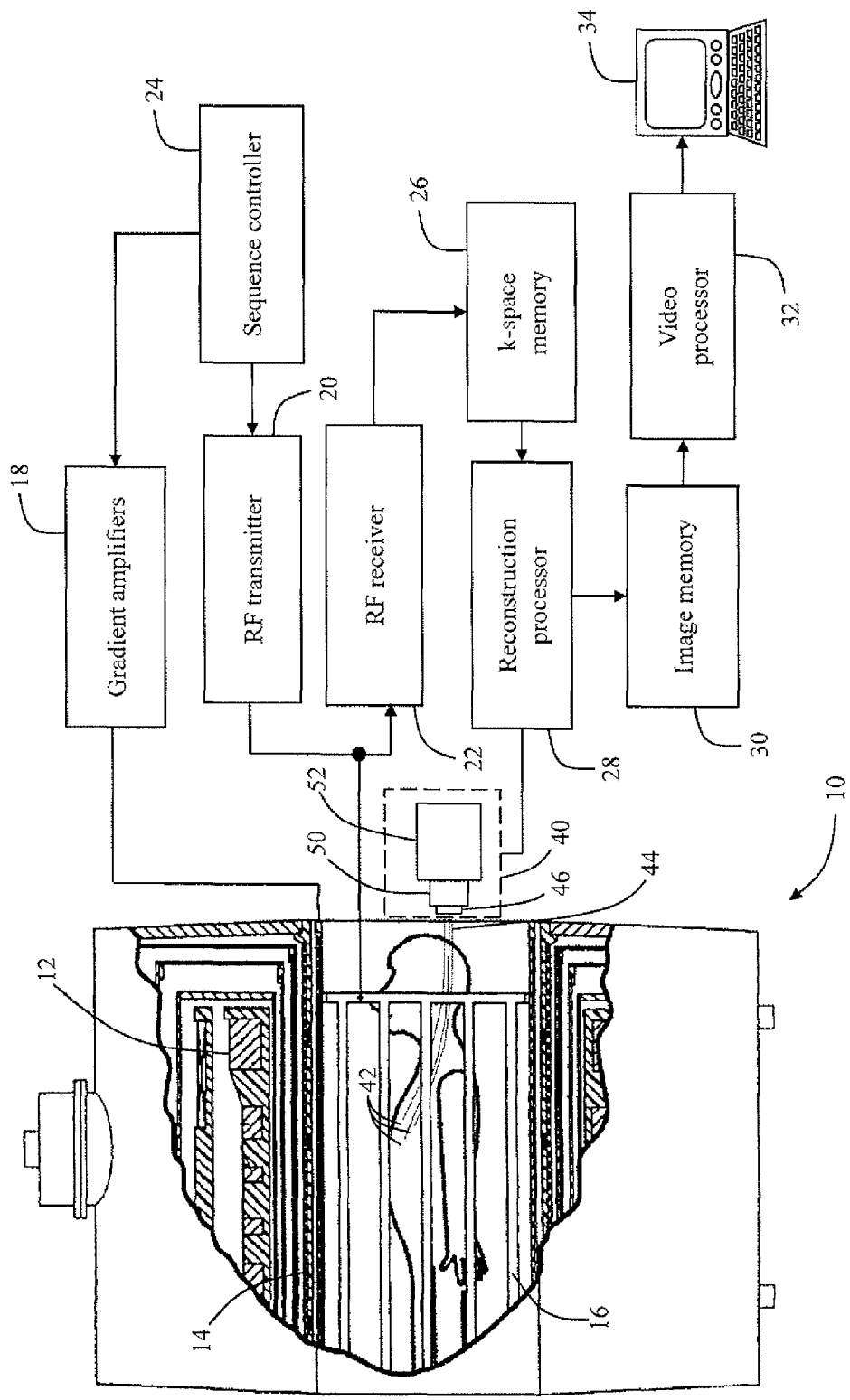
FIG. 1 is a diagrammatic illustration of a magnetic resonance imager with an MR compatible ECG monitor.

With reference to FIG. 1, a magnetic resonance scanner 10 is depicted. The magnetic resonance scanner 10 is illustrated as a closed bore system that includes a solenoidal main magnet assembly 12, although open and other magnet configurations are also contemplated. The main magnet assembly 12 produces a substantially constant main magnetic field oriented along a horizontal axis of an imaging region. It is to be understood that other magnet arrangements, such as vertical, and other configurations are also contemplated. The main magnet 12 in an bore type system may have a field strength of around 0.5 T to 7.0 T or more. The 5 Gauss line is typically closer at lower field strengths and further at high field strengths, but can also vary with other factors such as shielding and configuration.

A gradient coil assembly 14 produces magnetic field gradients in the imaging region for spatially encoding the main magnetic field. Preferably, the magnetic field gradient coil assembly 14 includes coil segments configured to produce magnetic field gradient pulses in three orthogonal directions, typically longitudinal or z, transverse or x, and vertical or y directions.

A radio frequency coil assembly 16 generates radio frequency pulses for exciting resonance in dipoles of the subject. The radio frequency coil assembly 16 depicted in FIG. 1 is a whole body birdcage type coil. The radio frequency coil assembly 16 also serves to detect resonance signals emanating from the imaging region. The radio frequency coil assembly 16 is a send/receive coil that images the entire imaging region, however, local send/receive coils or local dedicated receive coils are also contemplated.

Gradient pulse amplifiers 18 deliver controlled electrical currents to the magnetic field gradient assembly 14 to produce selected magnetic field gradients. A radio frequency transmitter 20, preferably digital, applies radio frequency pulses or pulse packets to the radio frequency coil assembly 16 to excite selected resonance. A radio frequency receiver 22 is coupled to the coil assembly 16 or separate receive coils to receive and demodulate the induced resonance signals.

To acquire resonance imaging data of a subject, the subject is placed inside the imaging region. A sequence controller 24 communicates with the gradient amplifiers 18 and the radio frequency transmitter 20 to supplement the optical manipulation of the region of interest. The sequence controller 24, for example, produces selected repeated echo steady-state, or other resonance sequences, spatially encode such resonances, selectively manipulate or spoil resonances, or otherwise generate selected magnetic resonance signals characteristic of the subject. The generated resonance signals are detected by the RF coil assembly 16 or local coil (not shown), communicated to the radio frequency receiver 22, demodulated, and stored in a k-space memory 26. The imaging data is reconstructed by a reconstruction processor 28 to produce one or more image representations that are stored in an image memory 30. In one suitable embodiment, the reconstruction processor 28 performs an inverse Fourier transform reconstruction.

The resultant image representation(s) is processed by a video processor 32 and displayed on a user interface 34 equipped with a human readable display. The interface 34 is preferably a personal computer or workstation. Rather than producing a video image, the image representation can be processed by a printer driver and printed, transmitted over a computer network or the Internet, or the like. Preferably, the user interface 34 also allows a radiologist or other operator to communicate with the sequence controller 24 to select magnetic resonance imaging sequences, modify imaging sequences, execute imaging sequences, and so forth.

An electrocardiogram (ECG or EKG) monitor 40 is also present in the MR suite. The ECG monitor receives electrical readings from electrodes 42 placed at characteristic pickup points on the patient's chest, side, back, and legs. Electrical signals are transmitted over a series of leads 44. The leads 44 are gathered and terminated in a plug 46 that can plug into a connector 50 of the monitor 40. The connector 50 is in turn electronically and physically connected to a printed circuit board (PCB) 52 of the monitor 40 as described below. Alternately, the electrodes 42 may have the ability to wirelessly communicate data to the monitor 40. In this case, the plug 46 would connect to a connector 50 of a transmitter module circuit board, e.g. and RF, optical, or like transmitter. A suitable receiver would be connected to the ECG monitor 40. Such an RF transmitter would operate in a frequency range well outside the operating range of the RF assembly 16, to avoid interference with the RF signals. The user can request ECG readings or printouts from the monitor 40 as desired. Additionally, the ECG monitor may be in communication with the reconstruction processor 28 for reconstructing cardiac gated images, and the like.

Figure 2:
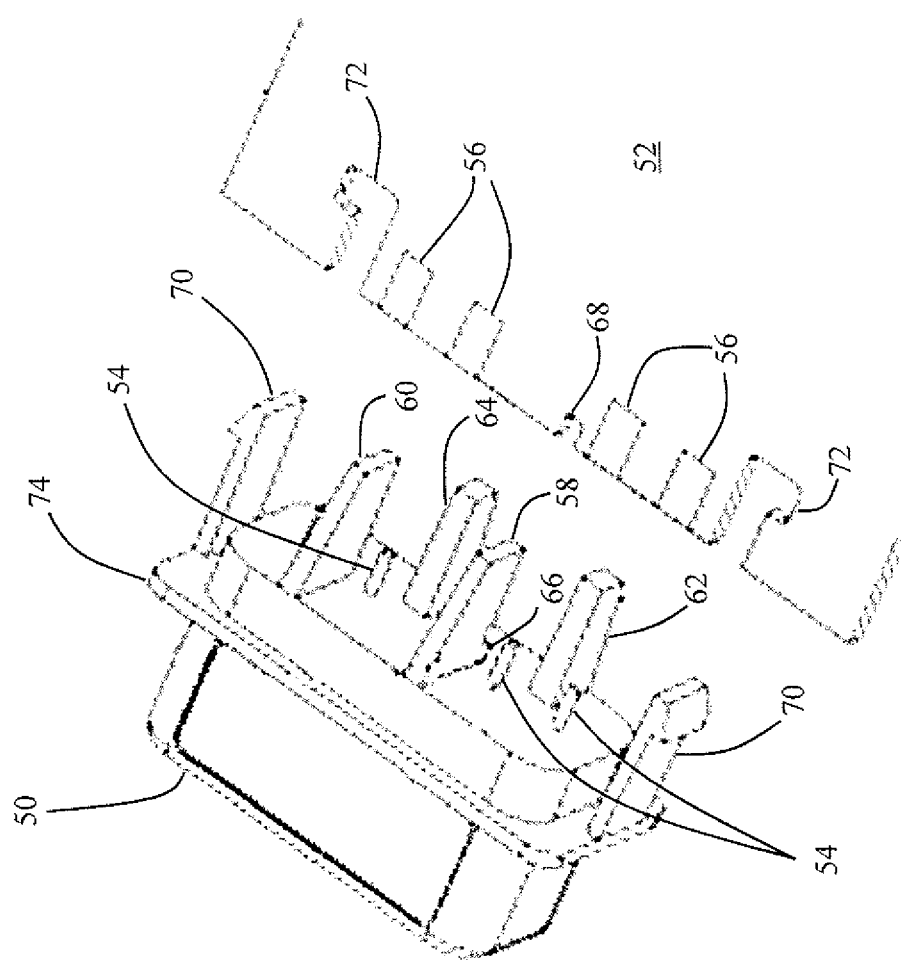
FIG. 2 is an expanded view of a lead wire connector and a printed circuit board.
Figure 3:
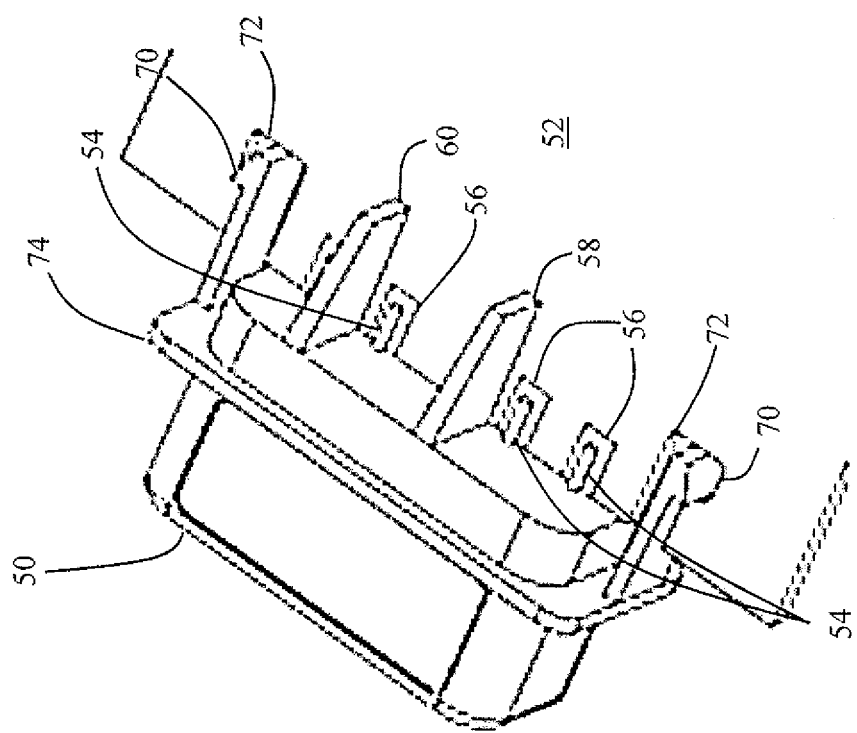
FIG. 3 depicts the lead wire connector of FIG. 2 connected to the printed circuit board.
Figure 4:
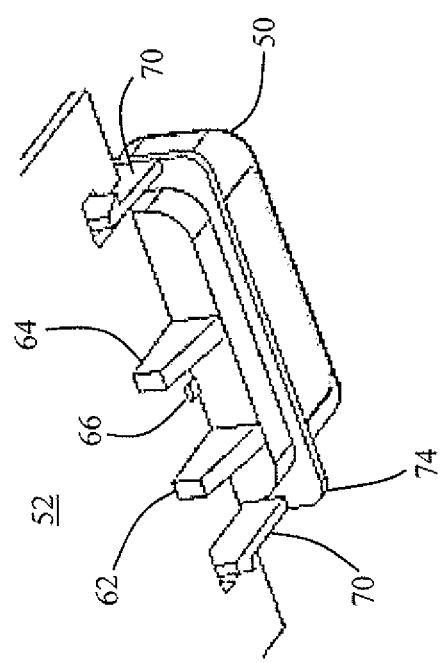
FIG. 4 depicts the lead wire connector connected to the printed circuit board as seen from underneath the circuit board.
Figure 5:
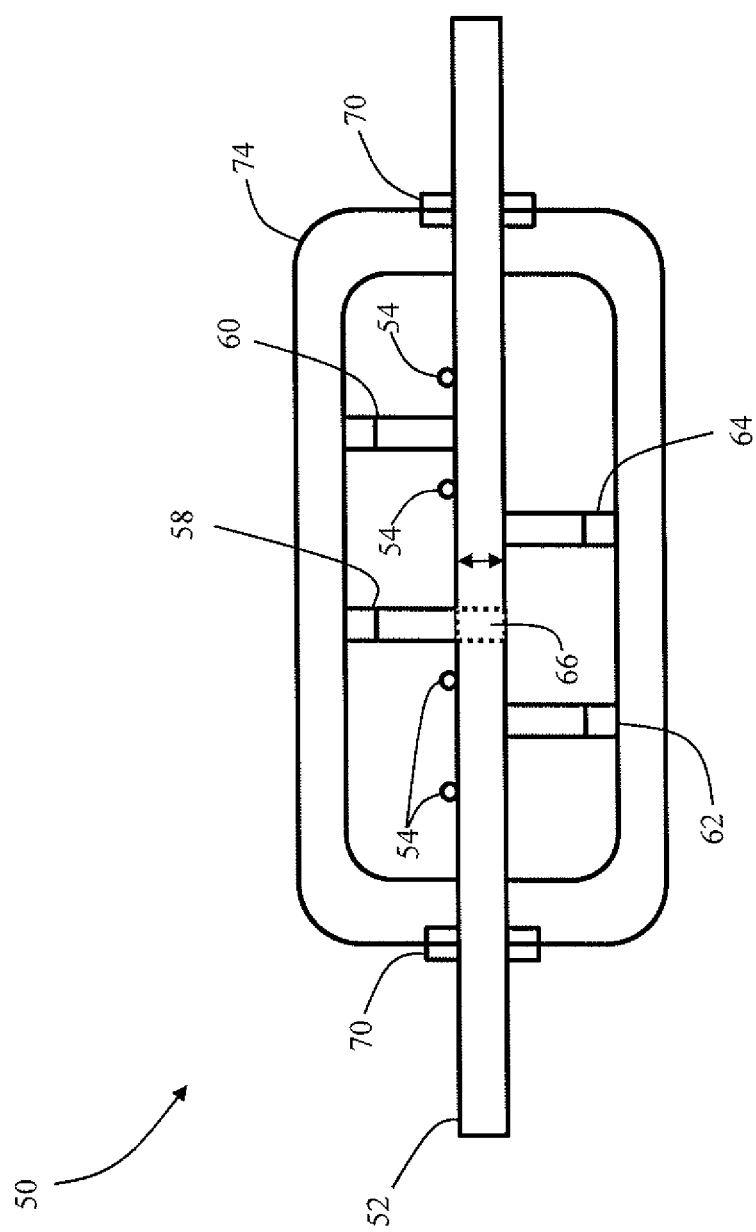
FIG. 5 is a head-on view of the connector.

With reference now to FIGS. 2, 3, and 4 the connector 50, and how it interfaces with the PCB 52 is described in more detail. Electrical connector pins 54 contact respective solder pads 56. Upper tabs 58, 60 and lower tabs 62, 64 help align the connector 50 in a vertical dimension to the PCB 52, and later help secure the connector 50 to the PCB 52. A vertical distance between the upper tabs 58, 60 and the lower tabs 62, 64 (as indicated by the arrow in FIG. 5) is substantially the width of the PCB 52. Thus the tabs 58, 60, 62, 64 frictionally grip the PCB 52 snugly and prevent vertical movement and canting of the connector 50 relative to the PCB 52 once the connector 50 has been attached to the PCB 52 as depicted in FIG. 3. The horizontal length of the tabs 58, 60, 62, 64 is selected to prevent pitching of the connector 50 relative to the PCB 52 without sacrificing significant space on the PCB 52 available for circuit components. In addition to preventing pitch of the connector 50, the tabs 58, 60, 62, 64 prevent the connector 50 from rolling relative to the PCB 52. Working in conjunction, the tabs 58, 60, 62, 64 lock down three degrees of movement of the connector 50 relative to the PCB 52, namely vertical motion, pitch and roll.

Located on the underside of the tab 58, is a tab extension 66. In the illustrated embodiment, the tab extension has a vertical height that is the same as the width of the circuit board, as indicated by the arrows in FIG. 5. The tab extension 66 serves to align the connector 50 in a transverse direction to the PCB 52. The tab extension 66 fits into a notch 68 in the PCB 52. The tab extension 66 is positioned in the plane of the PCB 52. Only when the connector 50 is both transversely and vertically aligned to the PCB 52 will the tab extension 66 fit into the notch 68. If the connector 50 is not vertically aligned, then the PCB 52 will not pass between the tabs 58, 60, 62, 64, preventing the tab extension 66 from reaching the notch 68. When the tab extension 66 successfully mates with the notch 68, the pins 54 are in robust contact with the solder pads 56, as shown in FIG. 3. Also when the tab extension 66 is mated with the notch 68, the connector 50 is prevented from translating along the edge of the PCB 52. The tab extension 66 and notch 68 lock down the fourth degree of motion.

The last two degrees of motion, i.e., translation away from the PCB 52 and yawing of the connector 50 relative to the PCB 52 are locked down by a pair of snap hooks 70. Each snap hook 70 fits into a respective snap lock 72 in the PCB 52. The snap hooks 70 can only begin to mate with the snap locks 72 when the connector 50 is vertically aligned. Otherwise, the tabs 58, 60, 62, 64 would prevent the snap hooks 70 from starting to mate with the snap locks 72. The snap hooks 70 can only fully mate with the snap locks 70 and hence, snap into position, when the tab extension 66 is mated with the notch 68. Alternately, the snap hooks 70 could be in the plane of the PCB 52 rather than perpendicular thereto as illustrated. The snap locks 72 would change in orientation to accommodate. When the snap hooks 70 lock into position, all six degrees of motion of the connector 50 are locked down. The pins 54 are then soldered or otherwise electrically connected to the solder pads 56.

As the connecting pins 54 are aligned parallel to the solder pads 56, 90° angles are eliminated from the conducting paths, making the circuit less vulnerable to electromagnetic interference intrusions. The tab 58 and the tab extension 66 are intentionally located off center between the snap hooks 70 to prevent installing the connector upside-down. Thus, it is impossible to line up both the snap hooks 70 with the snap locks 72 and the tab extension 66 with the notch 68 unless orientation of the connector 50 relative to the PCB 52 is correct. If an assembler attempts to attach the connector 50 upside-down, the tab extension 66 will not mate with the notch 68.

The connector 50 also includes a flange 74 onto which the exterior housing of the monitor 40 can seal to further insulate the solder connections from mechanical stressors such as removal/insertion of the plug 46 into the connector 50, inadvertent drops, and vibrations.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A magnetic resonance system comprising:
 a main magnet for generating a substantially uniform main magnetic field in an examination region;
 a gradient coil assembly for imposing gradient magnetic fields on the main magnetic field in the examination region, spatially encoding the main magnetic field;
 a radio frequency assembly for inducing magnetic resonance in selected dipoles of a subject in the examination region, and receiving the magnetic resonance;
 a monitor for analyzing signals originating from sensors in the examination region, the monitor including a connector for providing an interface between sensor leads and a printed circuit board within the monitor, the connector including:
  electrical connector pins which are parallel to and mate with solder pads of the circuit board adjacent an edge of the circuit board;
  upper tabs and lower tabs that engage upper and lower surfaces of the circuit board and are staggered such that the upper and lower tabs prevent vertical movement, pitching, and rolling of the connector relative to the circuit board;
  first and second snap hooks that engage snap locks in the circuit board that prevent separation of the connector and circuit board and prevent yawing of the connector relative to the circuit board; and
  a tab extension extending from one of the tabs that engages a notch in the circuit board and prevents transverse movement of the connector relative to the circuit board, the tab extension being offset between the snap hooks such that the snap hooks cannot engage the snap locks unless the tab extension engages the notch, the tab extension further being of the same width as the one of the tabs from which it extends.

2. The magnetic resonance system as set forth in claim 1, wherein the monitor is an electrocardiogram monitor.

3. The magnetic resonance system as set forth in claim 1, wherein a first upper tab is off-center relative to edges of the connector.

4. The magnetic resonance system as set forth in claim 1, wherein the connector further includes:
 a tab that engages a notch in the circuit board to provide transverse alignment and prevent transverse movement of the connector relative to the circuit board.

5. The connector as set forth in claim 1, wherein the electrical connector pins are straight.

6. A method of monitoring a subject in a magnetic field comprising:
 placing electrodes on the patient;
 connecting leads to the electrodes;
 plugging the leads into a connector having connector pins that are parallel to and frictionally engage with solder contacts on a surface of a circuit board of a monitor;
 preventing the connector from translating vertically, rolling, and yawing with respect to the circuit board with at least first and second upper tabs and first and second lower tabs, the upper and lower tabs being staggered such that the upper tabs are not aligned with the lower tabs;
 preventing the connector from translating along an edge of the circuit board by mating a tab extension with a notch in the circuit board, the tab extension having the same width as and extending from at least one of the first upper tab, second upper tab, first lower tab, and second lower tab;
 generating a main magnetic field with a main magnet of a magnetic resonance imaging device;
 applying gradient magnetic fields to the examination region with a gradient coil system;
 applying RF pulses to the examination region with an RF assembly; and
 communicating information from the sensors to the monitor over the leads that interface with the monitor via the connector; and
 wherein the connector does not introduce angular changes in a conductive path between the solder contacts and the leads.

7. The method as set forth in claim 6, further including:
 engaging upper tabs and lower tabs of the connector with upper and lower surfaces of the circuit board to prevent vertical movement, pitching, and rolling of the connector relative to the circuit;
 mating first and second snap hooks with snap locks in the circuit board preventing yawing of the connector relative to the circuit board and preventing the connector from pulling away from the circuit board; and
 engaging a tab extension from one of the tabs with a notch in the circuit board and preventing transverse movement of the connector relative to the circuit board, the tab extension being off center between the snap hooks such that the snap hooks cannot engage the snap locks unless the tab extension engages the notch.

8. An edge connector comprising:
 upper tabs which engage an upper surface of a printed circuit board;
 lower tabs which engage a lower surface of the printed circuit board, the upper and lower tabs cooperating to hold the connector against vertical displacement, pitching, and rolling;
 connector pins extending parallel to the circuit board for electrical connection to solder pads on the circuit board at an edge of the circuit board;
 first and second snap hooks configured to engage snap locks in the circuit board to prevent separation of the connector and circuit board and prevent yawing of the connector relative to the circuit board;
 a tab extension of the same width as and extending from one of the tabs configured to engage a notch in the circuit board to prevent transverse movement of the connector relative to the circuit board, the tab extension being located off center between the snap hooks to prevent the snap hooks from engaging the snap locks unless the tab extension engages the notch.

9. The connector as set forth in claim 8, wherein the hooks and latches are perpendicular to the circuit board.

10. An ECG monitor including electrical circuitry on the printed circuit board and the connector as set forth in claim 8 for receiving ECG electrode leads.

11. The ECG monitor as set forth in claim 10 further including:
   an ECG lead set which connects at one end with ECG electrodes and at the other end plugs into the connector.

12. An MRI system comprising:
   a main magnet for generating a substantially uniform main magnetic field in an examination region;
   a gradient coil assembly for imposing gradient magnetic fields on the main magnetic field in the examination region, spatially encoding the main magnetic field;
   a radio frequency assembly for inducing magnetic resonance in selected dipoles of a subject in the examination region, and receiving the magnetic resonance;
   the ECG monitor as set forth in claim 10.

13. The MRI system as set forth in claim 12, further including:
   an image reconstruction processor, the image reconstruction processor being connected to the ECG monitor to reconstruct images in accordance with cardiac phase.

14. An electrocardiogram monitor for use in areas with magnetic or RF fields comprising:
   at least one printed circuit board that carries operational electronics of the monitor;
   a connector to decrease potential interference with ECG signals by the RF fields for connecting external sensor leads to the circuit board, the connector including:
      straight connector pins that tangentially engage an edge of the circuit board at solder pads;
      upper tabs and lower tabs that are staggered such that the upper tabs do not align with the lower tabs to prevent vertical movement, pitching, and rolling of the connector relative to the circuit board;
      a tab extension located off center with respect to the edges of the connector that mates with a notch in the circuit board for preventing sliding of the connector along the edge of the circuit board;
      snap hooks that prevent yawing of the connector with respect to the circuit board, and prevent the connector from pulling away from the circuit board when the snap hooks are mated with snap locks of the circuit board; and
      a flange onto which an exterior housing of a monitor can seal to further insulate the solder connections from mechanical stressors.

* * * * *